United States Patent
Maznev et al.

(10) Patent No.: US 7,327,468 B2
(45) Date of Patent: Feb. 5, 2008

(54) OPTO-ACOUSTIC APPARATUS WITH OPTICAL HETERODYNING FOR MEASURING SOLID SURFACES AND THIN FILMS

(75) Inventors: Alexei Maznev, Natick (RU); Zhuoyun Li, Shrewsbury, MA (US); Alexander Mazurenko, Dedham, MA (US)

(73) Assignee: Advanced Metrology Systems LLC, Natick, MA (US)

( * ) Notice: Subject to any disclaimer, the term of this patent is extended or adjusted under 35 U.S.C. 154(b) by 218 days.

(21) Appl. No.: 10/484,584

(22) PCT Filed: Jul. 26, 2002

(86) PCT No.: PCT/IB02/02918

§ 371 (c)(1),
(2), (4) Date: Jan. 22, 2004

(87) PCT Pub. No.: WO03/010518

PCT Pub. Date: Feb. 6, 2003

(65) Prior Publication Data
US 2004/0174529 A1 Sep. 9, 2004

Related U.S. Application Data

(60) Provisional application No. 60/307,905, filed on Jul. 26, 2001.

(51) Int. Cl.
*G01B 11/02* (2006.01)
*G01B 9/02* (2006.01)
*G02B 5/18* (2006.01)
*G02B 27/44* (2006.01)

(52) U.S. Cl. .................. 356/504; 356/521

(58) Field of Classification Search ............ 356/484, 356/485, 486, 502, 503, 504, 521
See application file for complete search history.

(56) References Cited

U.S. PATENT DOCUMENTS

| 4,472,053 | A | * | 9/1984 | Wyatt et al. | 356/121 |
|---|---|---|---|---|---|
| 5,734,470 | A | | 3/1998 | Rogers et al. | 356/354 |
| 5,748,317 | A | * | 5/1998 | Maris et al. | 356/502 |
| 5,812,261 | A | * | 9/1998 | Nelson et al. | 356/318 |
| 6,069,703 | A | | 5/2000 | Banet et al. | 356/432 |
| 6,204,926 | B1 | * | 3/2001 | Maznev et al. | 356/521 |
| 6,256,100 | B1 | | 7/2001 | Banet et al. | 356/432 |

FOREIGN PATENT DOCUMENTS

WO WO 0109586 2/2001

* cited by examiner

*Primary Examiner*—Michael A. Lyons
(74) *Attorney, Agent, or Firm*—Goodwin Procter LLP

(57) ABSTRACT

In an opto-acoustic measuring device for thin films and solid surfaces, the probe beam is split into a first probe beam portion and a second reference beam portion. The splitting of the probe beam is achieved using a phase mask that also splits the excitation beam. The probe beam is aligned using a retro-reflector on a motorized stage to control the beam angle. Excitation and probe/reference beams are overlapped at the sample surface. The first probe beam portion gets diffracted by material disturbances generated by excitation beams. The diffracted part of the first probe beam portion is collinear with the second reference beam portion, resulting in heterodyning. The heterodyne signal measured by the detector is analyzed in order to determine thickness and/or other properties of a thin film or solid surface. The invention improves magnitude and reproducibility of the opto-acoustic signal which results in enhanced precision of measurements.

41 Claims, 11 Drawing Sheets

DETAIL 1

DETAIL 2

DETAIL 3.
CROSS-SECTION THROUGH BEAM
PATH BETWEEN LENS PAIR (7),
SHOWING ALL FOUR BEAMS.
(CROSS-REFERENCE FIG. 2)

DETAIL 4.
DETECTOR APERTURE (11) WITH
SWITCHABLE APERTURE (12)
BEHIND IT.
(CROSS-REFERENCE FIG. 2)

$$\Delta z = \Lambda/2\tan(\delta) \quad (6) \quad \}\text{FIG. 11J}$$

$$\sin\theta/2 = \lambda/2\Lambda \quad (7) \quad \}\text{FIG. 11K}$$

$$X = X_0 + f\tan\theta \quad (8) \quad \}\text{FIG. 11L}$$

$$\delta_{AF} = \theta_5 - \theta_{12} \quad (9) \quad \}\text{FIG. 11M}$$

$$\theta_{AF} = 2\theta_5 - \theta_{12} \quad (10) \quad \}\text{FIG. 11N}$$

$$I_S = I_D + I_R + 2\sqrt{I_D I_R}\cos\phi \quad (1)$$

FIG. 11A $$\Lambda = \frac{\lambda_{e,p}}{2\sin(\theta_{e,p}/2)} \quad (2)$$

FIG. 11B

| | |
|---|---|
| EXCITATION LASER - (2) - (5) | 100 mm, 26 mm |
| (5) - (7) - (7) - SAMPLE | 75 mm, 87 mm, 75 mm |
| SAMPLE - (10) - DETECTOR | 100 mm, 100 mm |
| PROBE LASER - (3) - (5) | 100 mm, 80 mm |

FIG. 11C $$\frac{I_N}{I_0} = \left(\frac{\sin(\pi N/2)}{\pi N/2}\right)^2 \frac{1 \pm \cos[2\pi d(n-1)/\lambda)]}{2} \quad (3)$$

FIG. 11D $$I_{oddNmax}/I_0 = 4/\pi^2 N^2$$

FIG. 11E $$d = \frac{\lambda_p}{(n-1)} = 1833\text{ nm} \quad (4)$$

FIG. 11F

| | |
|---|---|
| ZERO ORDER @ 830 ± 10 nm | >99.85% |
| 1st ORDER @ 830 ± 10 nm | <0.06% |
| 1st ORDER @ 532 | 37.5% (= 92.7% OF OPTIMAL) |

FIG. 11G

| | |
|---|---|
| ZERO ORDER @ 830 ± 10 nm | >98% |
| 1st ORDER @ 830 ± 10 nm | <0.7% |
| 1st ORDER @ 532 | 33.6% (= 83% OF OPTIMAL) |

FIG. 11H $$\phi = qz\tan(\delta) \quad (5)$$

FIG. 11I

| MEASURED SAMPLE/ STRUCTURE | REPEATABILITY OF A PRIOR ART SYSTEM (Å) | REPEATABILITY OF THE HETERODYNE SYSTEM (Å) |
|---|---|---|
| 4000 Å-THICK Cu, 50x100 μm TEST PAD | 60.5 | 5.0 |
| 4000 Å-THICK Cu, 50x50 μm TEST PAD | 87.8 | 15.6 |
| 4000 Å-THICK Cu DAMASCENE ARRAY (0.5 μm Cu LINES SEPARATED BY 0.5 μm SiO₂) IN A 50x100 μm TEST PAD | 107.4 | 3.3 |
| 12000 Å ELECTROPLATED Cu FILM WITH ROUGH SURFACE, BLANKET WAFER | 159.1 | 46.3 |
| 225 Å-THICK Ta, BLANKET WAFER | 4.1 | 0.8 |

FIG. 13

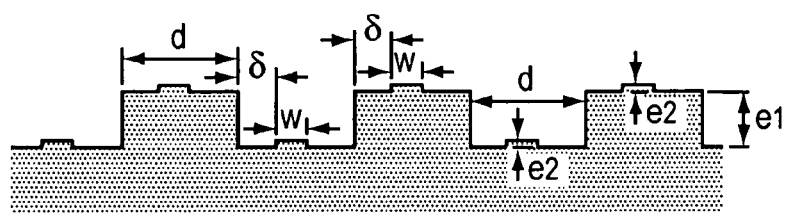

"POSITIVE" DUAL-ETCH PATTERN

FIG. 14A

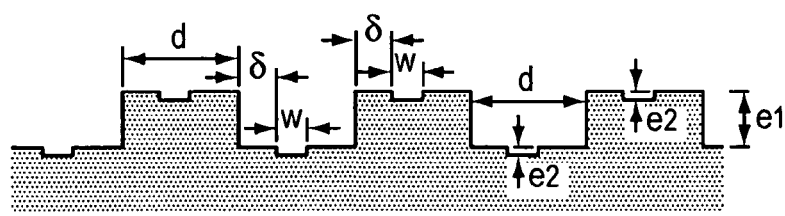

"NEGATIVE" DUAL-ETCH PATTERN

FIG. 14B

| PATTERN # | PM PERIOD μm | WIDTH w, μm | PRIMARY ETCH DEPTH e1, μm | SECONDARY ETCH DEPTH e2, μm |
|---|---|---|---|---|
| 1 | 15.50 | 5.425 | 1.732 | 0.130 |
| 2 | 48.42 | 14.526 | | |
| 3 | 29.05 | 8.715 | | |
| 4 | 21.95 | 7.683 | | |
| 5 | 13.43 | 1.343 | | |
| 6 | 8.97 | 1.000 | | |
| 7 | 7.81 | 1.000 | | |
| 10 | 10.65 | 1.065 | | |
| 11 | 17.68 | 6.188 | | |
| 12 | 25.18 | 7.554 | | |
| 13 | 35.51 | 10.653 | | |
| 14 | 58.75 | 17.625 | | |
| 15 | 72.00 | 21.600 | | |

OPTO-ACOUSTIC APPARATUS WITH OPTICAL HETERODYNING FOR MEASURING SOLID SURFACES AND THIN FILMS

RELATED PATENTS AND APPLICATIONS

The present application claims benefit of provisional application No. 60/307,905 filed Jul. 26, 2001, which is incorporated herein by reference.

The following applications and patents are also incorporated herein by reference:
A. U.S. patent application Ser. No. 09/087,141 filed May 28, 1998;
B. U.S. Ser. No. 08/783,046 (entitled METHOD AND DEVICE FOR MEASURING THE THICKNESS OF OPAQUE AND TRANSPARENT FILMS)
C. U.S. Pat. No. 6,393,915 Method and device for simultaneously measuring multiple properties of multilayer films
D. U.S. Pat. No. 6,348,967 Method and device for measuring the thickness of opaque and transparent films
E. U.S. Pat. No. 6,256,100 Method and device for measuring the thickness of thin films near a sample's edge and in a damascene-type structure
F. U.S. Pat. No. 6,188,478 Method and apparatus for film-thickness measurements
G. U.S. Pat. No. 6,175,421 Method and apparatus for measuring material properties using transient-grating spectroscopy
H. U.S. Pat. No. 6,122,064 Method for measuring thickness of films
I. U.S. Pat. No. 6,118,533 Method and apparatus for measuring the concentration of ions implanted in semiconductor materials
J. U.S. Pat. No. 6,081,330 Method and device for measuring the thickness of opaque and transparent films
K. U.S. Pat. No. 6,075,602 Method and apparatus for measuring material properties using transient-grating spectroscopy
L. U.S. Pat. No. 6,069,703 Method and device for simultaneously measuring the thickness of multiple thin metal films in a multilayer structure
M. U.S. Pat. No. 6,052,185 Method and apparatus for measuring the concentration of ions implanted in semiconductor materials
N. U.S. Pat. No. 6,016,202 Method and apparatus for measuring material properties using transient-grating spectroscopy
O. U.S. Pat. No. 5,982,482 Determining the presence of defects in thin film structures
P. U.S. Pat. No. 5,812,261 Method and device for measuring the thickness of opaque and transparent films
Q. U.S. Pat. No. 5,734,470 Device and method for time-resolved optical measurements
R. U.S. Pat. No. 5,672,830 Measuring anisotropic mechanical properties of thin films
S. U.S. Pat. No. 5,633,711 Measurement of material properties with optically induced phonons
T. U.S. Pat. No. 5,546,811 Optical measurements of stress in thin film materials
U. U.S. Pat. No. 5,394,413 (entitled PASSIVELY Q-SWITCHED PICOSECOND MICROLASERS; describes a small-scale "microlaser" that can be used to form excitation pulses)

BACKGROUND OF THE INVENTION

A. Field of the Invention

The invention relates to the field of opto-acoustic measurement of thin films and solid surfaces.

B. Related Art

Impulsive Stimulated Thermal Scattering ("ISTS") measurement of thin films is known from the Philips Impulse/Emerald products. ISTS, a form of opto-acoustic measurement, is advantageous in being able to measure thin film and solid surface properties quickly and nondestructively as part of an assembly line process.

SUMMARY OF THE INVENTION

It has been discovered that in ISTS measurements at solid surfaces and of thin films, the signal intensity is typically very small, on the order of $10^{-5}$-$10^{-6}$ of the intensity of the probe beam incident on the sample. This fact adversely affects precision of ISTS measurements of sample parameters, such as thin film thickness, particularly on samples with low thermal expansion such as silicon, or very thin (<300 Å) metal films. Another problem, specific to measurement of solid surfaces and thin films, is the presence of surface roughness resulting in scattering of the probe light. Scattered light coherently interferes with the useful signal resulting in an increase of the signal amplitude but making it extremely irreproducible. Finely patterned structures fabricated at the sample surface also scatter probe light making it difficult to use ISTS for measurements on product wafers in the semiconductor industry.

It would be desirable to improve the repeatability and precision of opto-acoustic measurements of thin films and/or solid surfaces, particularly on samples with surface roughness and/or finely patterned structure.

Advantageously, repeatability of opto-acoustic measurements is improved via optical heterodyning. Preferably, the probe beam is advantageously split into probe and reference beam portions and the optical system ensures that the reference beam propagates together with the diffracted signal to the detector. Preferably, the splitting of the probe beam is performed using the same phase grating that splits the excitation beam into two portions. The phase grating should be is designed for optimized performance at excitation and probe wavelengths. The optical layout should allow insertion of a vision system. Preferably, also, a retroreflector, disposed on a movable stage, is used to align the probe beam.

Objects and advantages of the invention will be apparent in the following.

BRIEF DESCRIPTION OF THE DRAWING

FIGS. 11A-N show equations and tables referred to in the text.

FIG. 13 shows repeatability of thickness measurements on thin films and structures fabricated on silicon wafers achieved with a prior art apparatus and with the heterodyne system.

FIGS. 14A&B show cross-sections of dual-etch phase masks representing two possible versions of the design.

Figure 1A:
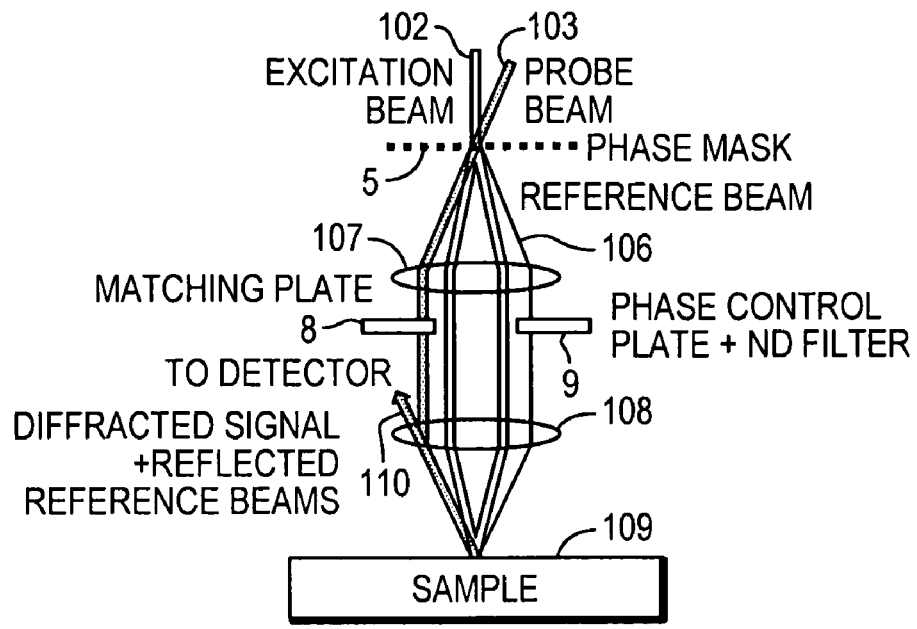
FIG. 1A shows a front view of the principal schematic of the heterodyne setup.

DETAILED DESCRIPTION OF THE PREFERRED EMBODIMENTS 1.0 Introduction

In the prior art (refs. A and R-T, above), ISTS measurement of thin film thickness and/or properties was performed by exciting surface acoustic wave (SAW) at the sample surface by two laser pulses (excitation pulses) and measuring its frequency by detecting the diffraction of the third laser beam (probe beam). A problem in the ISTS measurements was poor repeatability of film thickness measurement on samples yielding particularly small signal (e.g. metal films less than 300 Å in thickness, or dielectric films on silicon) as well as on samples resulting in a significant scattering of the probe light off surface roughness and/or edges of structures on patterned wafers. As will be discussed below, optical heterodyne detection of the ISTS signal was implemented in order to enhance the signal level and thus increase the repeatability of the measurements.

Heterodyne detection is achieved by using a fourth laser beam (reference beam) coherent with the probe beam and propagating collinear with the diffracted signal. The optical intensity at the detector $I_S$ is a result of the coherent interference of the diffracted signal $I_D$ and reference beam $I_R$ and is given by equation (1) of FIG. 11A, where φ is the phase difference between the diffracted probe and reference beams. Typically, the reference beam is much more intense than the diffracted signal. In this case, the transient signal measured by the detector is dominated by the third term of Eq. (1). Thus heterodyning allows one to enhance the magnitude of the signal. Although it does not increase the theoretical signal-to-noise limit determined by the photon statistics, it helps to suppress other sources of noise, relative to signal strength, such as detection electronics noise and parasitically scattered light. Heterodyning is most helpful with "difficult" samples, i.e. either those yielding low signal or excessive scattered light (e.g. due to rough surfaces or small test pad sizes on patterned wafers). Another advantage of optical heterodyning is signal linearity with respect to the displacement of the sample surface, which makes the appearance of the signal waveform more regular and easier to analyze.

Transient grating measurements in simple liquids with optical heterodyning attempted in the past had to deal with instability of the heterodyne phase, P. Vohringer and N. Scherer, "Transient Grating Optical Heterodyne Detected Impulsive Stimulated Raman Scattering in Simple Liquids", J. Phys. Chem. 99, 2684 (1995). Advantageously, this problem can be solved using the phase mask in order to produce both the excitation and probe/reference beam pairs, see A. A. Maznev et al. "Optical Heterodyne Detection of Laser-Induced Gratings," Opt. Lett. 23, 1319 (1998). This solution made the heterodyne setup extremely stable.

However, the optical set-up used by Maznev et al. was not suitable for a practical device for thin film measurements, and this type of measurement was not considered at that time. Maznev et. al. used first diffraction orders of the phase mask to produce both excitation and probe/reference beam pairs, with the phase mask etch depth corresponding to the optical path difference equal to one half of the optical wavelength. This scheme can work efficiently only if the probe and excitation wavelengths are close. As a result, Maznev et al. had to use a large laboratory argon-ion laser (wavelength 514 nm close to the excitation wavelength 532 nm) for the probe. This arrangement is incompatible with the practical thin film and solid surface measuring ISTS apparatus as described e.g. in M. Gostein et al., Thin-Film Metrology Using Impulsive Stimulated Thermal Scattering (ISTS), in Handbook of Silicon Semiconductor Metrology, ed. by A. C. Diebold (New York, Marcel Dekker, 2001), p.167, where a small diode laser (wavelength typically 830 nm) is used as a probe source. The set-up of Maznev et al. was also incompatible with automated control of the SAW wavelength via changing the phase mask patterns and thus varying the angle between the excitation beams and did not leave any space for a vision system. Thus the implementation of heterodyning for a practical thickness measurement apparatus required a complete redesign of the optical layout, developing a new phase mask design and the use of a retroreflector arrangement for the adjustment of the probe beam angle.

Section 2.0 Principal Schematic of the Heterodyne Setup

Figure 1B:
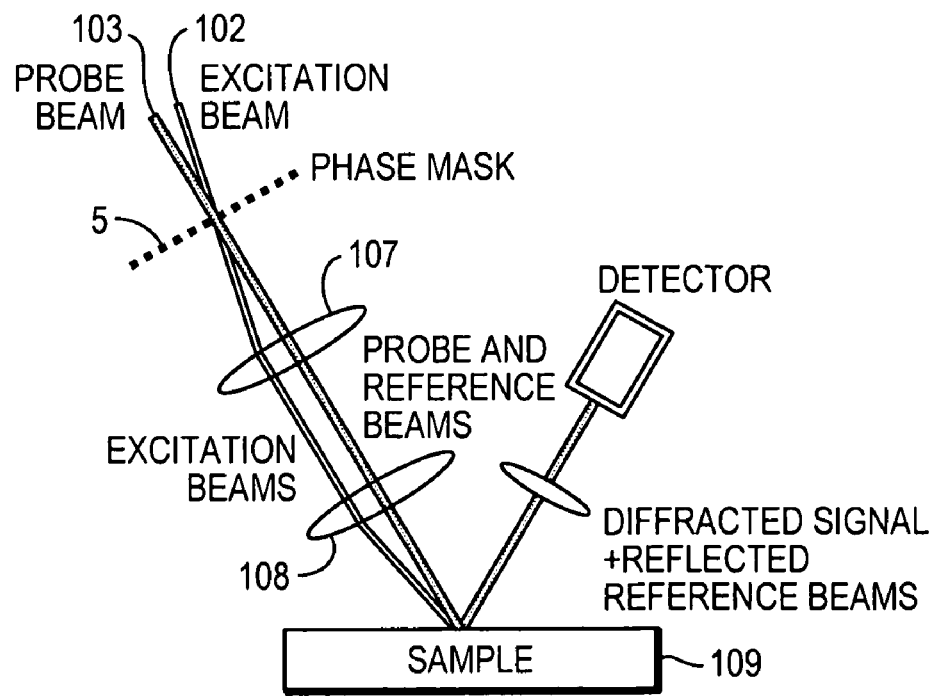
FIG. 1B shows a side view of the setup of FIG. 1A.

FIGS. 1A and 1B show the optical pathway in accordance with the invention along two perpendicular planes.

A diffractive element 5, below referred to as the "phase mask," is used to produce the excitation 102 and probe/reference 103 beam pairs. The beams from the excitation laser 102 (λ=532 nm, τ~0.5 ns) and the probe laser 103 (λ=830 nm, quasi-cw) are overlapped at the phase mask 5, as shown in FIG. 1. The phase mask 5 is designed in such a way (as discussed below, in section 5) that most of the excitation light is diffracted into the +/−1 diffraction orders (i.e., effectively the excitation beam 102 is split in two), while most of the probe beam 103 is transmitted into the zero order. Weak 2nd-order diffraction of the probe beam is used as a reference beam. The four beams are reconciled at the sample by a system of two achromatic lens assemblies 107, 108 imaging the plane of the phase mask 5 to the plane 109 of the sample surface. In one embodiment, the magnification of the optical system is approximately 1:1. In other embodiments, the magnification may be different, e.g. 1.5:1 and 4:1. In the latter embodiments with larger demagnification ratios, smaller periods at the sample are achieved without using substantially smaller phase mask periods, which would be more difficult to fabricate. The issue here is not only cost but also fabrication process limitations e.g. tolerances.

Interference of the excitation beams results in an intensity pattern at the sample 109 with period $\Lambda$ equal to ½ of the imaged phase mask period. The Equation 2 of FIG. 11B relates the period $\Lambda$ to the angle between a beam pair. In equation (2), $\lambda_{e,p}$ is the wavelength of the excitation or probe and $\theta_{e,p}$ is the angle between the excitation or probe/reference beams, respectively. By using multiple phase mask patterns, the period $\Lambda$ can be varied within the range 2-11 μm.

The reason that imaging of a fully transparent phase mask 5 results in a high-contrast intensity pattern at the sample lies in that higher-order diffraction beams (as well as the weak zero order) are blocked. In fact, with the phase masks used in the preferred embodiment, the $2^{nd}$-order beams are very weak and it is not necessary to block them as long as the $zero^{th}$ order is blocked, because they result in an interference pattern of twice the period of the main pattern and thus do not interfere with the latter. However, blocking the $3^{rd}$-order diffraction beams is necessary. If fixed apertures are used to block the $3^{rd}$-order beams, the possible wavelength range is then restricted to less than 3:1. (With motor-controlled beam blocks a wider range could be used). More about beam blocking in the preferred embodiment will be discussed below with respect to element 6 of FIG. 2.

Absorption of the excitation light at the sample surface 109 results in an impulsive spatially periodic temperature rise, which, in turn, gives rise to counter-propagating surface acoustic waves (SAWs) and a stationary thermal expansion pattern (thermal grating), all with the same period (wavelength) $\Lambda$. Both the SAWs and the thermal grating result in spatially periodic surface displacement (ripples) that causes diffraction of the probe beam. Since the ripple amplitude is typically very small (on the order of a few Å), only the first-order of the diffraction pattern is detectable.

The angle of diffraction off the laser-induced grating at the sample 109 matches the angle of the 2nd order diffraction off the phase mask, because the periods of the two gratings differ by a factor of two (times the demagnification of the imaging system). As a result the reflected reference beam 110 is always collinear with one of the diffraction orders of the probe beam as shown in FIG. 1A. Thus the detector will be monitoring the result of the coherent interference of the probe and reference beams, i.e. the heterodyne signal described by Eq. (1). A parameter defining the efficiency of heterodyning is the heterodyne phase $\theta$. This parameter is optimized by controlling the optical path of the reference beam via the angle of a plane-parallel optical element 9 inserted into the reference beam path, per FIG. 1A. The same optical element also has an attenuating filter, such as a neutral density ("ND") filter, coating attenuating the reference beam to a desired level ($\sim 10^{-4}$ with respect to the probe beam). An identical optical element 8 (but without ND filter coating, and without angle adjustability) is inserted into the probe beam path in order to preserve the coherence between the two beams.

It is desirable to make the heterodyne phase independent of the vertical position of the sample surface, to minimize sensitivity to focus variations. As shown in Section 8, that is preferably achieved by making the projections of the bisectors of the excitation and probe/reference beam pairs into the vertical plane identical, i.e. if both beam pairs are symmetric with respect to the vertical direction as viewed in FIG. 1A. Achieving this requires that the angle of incidence of the probe beam 103 on the phase mask 5 be adjusted for each phase mask period, as discussed in more detail below. As a result of the symmetry requirement, the signal beams (i.e. diffracted probe+reflected reference beams) propagate exactly in the direction of the incident probe beam as viewed in the projection on FIG. 1A. Another problem that can be gleaned from the view of FIG. 1A is that excitation beam blocks and optical elements in the probe and reference beam paths appear to be incompatible with a requirement that the angles between the beams vary in order to achieve a max to min SAW wavelength ratio of 5. Both problems are solved by separating the beams in the dimension perpendicular to the plane of the view of FIG. 1A, as illustrated by the side-view shown on the right of FIG. 1B. It should be noted that this "side-view" corresponds to the front view of the actual optical head (see Section 3). Thus the optical beam arrangement becomes 3-dimensional. FIG. 3C offers another illustration, which shows the position of the beams in a cross section along the optical path within the aperture of the imaging system between the two lenses.

3.0 Overview of the Optical Layout

Figure 2:
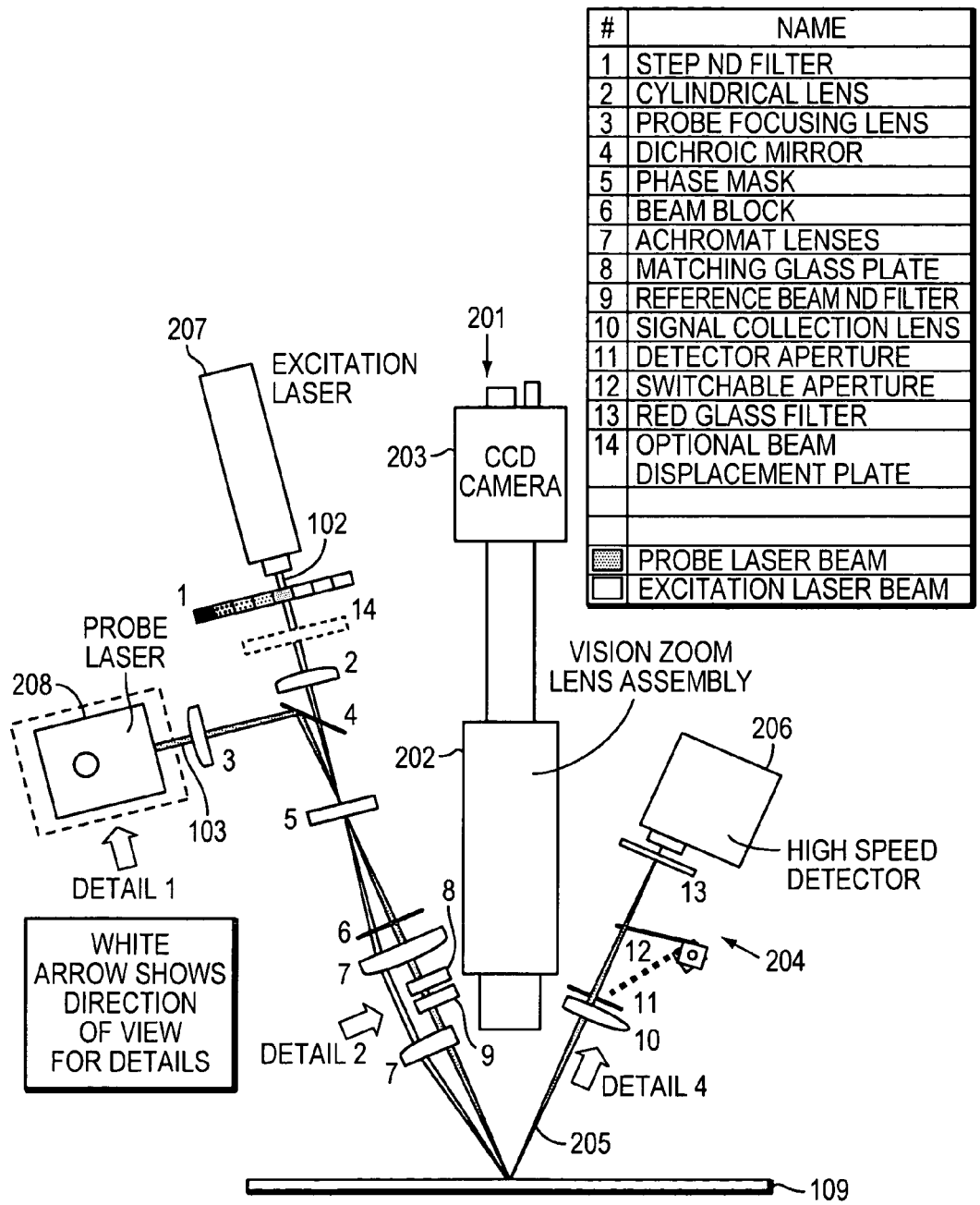
FIG. 2 shows a more detailed view of the optical head.

FIGS. 2 and 3 show the detailed optical layout of the preferred embodiment.

This layout follows the pattern of the sketches in FIG. 1. The biggest component is the vision system 201 including the zoom lens block 202 and the CCD camera 203 and located directly above the sample 109. The vision system is necessary for measurements on patterned wafers and is routinely used in semiconductor metrology. It allows the operator to view the sample surface and also helps to position the sample under the optics head in order to perform measurements in a specified point on the sample. Except for the sample positioning, the vision system does not take any part in the ISTS measurement process.

All the incident beam optics, including both lasers, are located to the left of the vision system 201. In addition to the basic optics shown in FIG. 1, both the excitation 102 and probe beams 103 pass though a number of other optical elements before reaching the phase mask, namely the step ND filter 1, the optional beam displacement plate 14, the cylindrical lens 2, the probe focusing lens 3, and the dichroic mirror 4. These elements attenuate the excitation beam and focus the excitation and probe beams to the desired size at the sample 103. The desired size is 300×50 μm for the excitation and 50×25 μm for the probe. These elements also provide a motorized control of the probe beam angle. In order to overlap the two beams, a dichroic 45° mirror 4 is used, reflecting the probe beam 103 and transmitting the excitation beam 102.

It is desirable to minimize the angle between the incident beams 102, 103 and the optical axis of the vision system 201, because this angle causes an undesirable dependence of the position of the laser spot within the field of view of the camera on the vertical position of the sample surface. On the other hand, it is desirable to preserve high numerical aperture of the vision system in order to achieve a vision system resolution of ~2 μm. As a result, the preferred embodiment uses a compromise angle of 16° between the optical axis of the camera 203 and the probe/reference beam bisector (not shown). Preferably the lenses 7 (referred to as 107 and 108 in FIGS. 1A&B) located next to the vision system are cut off to achieve this angle, as shown in FIG. 2. The angle between the planes containing the excitation and probe/reference beam pairs is ~3.5°.

The signal beam optics 204 are located to the right of the vision system 201 and are relatively simple: the signal 205 is focused on the detector 206, the reflected probe beam passes through signal collection lens 10 and is then blocked by the detector aperture (item 11 in FIG. 2), and scattered excitation light is cut off by a filter 13. An additional switchable or movable aperture (item 12 in FIG. 2) is used to reduce the amount of the parasitically scattered probe light (see Section 10.0).

Distances along the optical path between various components are as listed in the table of FIG. 11C.

Figure 3A:
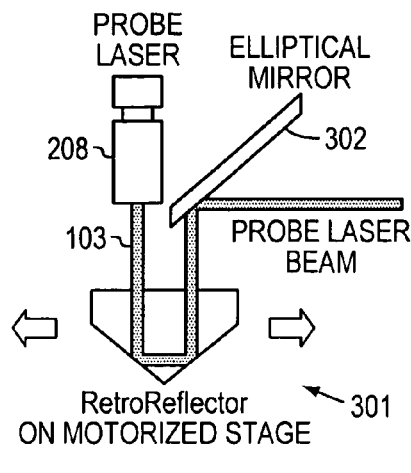
FIG. 3A shows a first detail expansion from FIG. 2

FIG. 3A will be discussed in section 7.0, below.

Figure 3B:
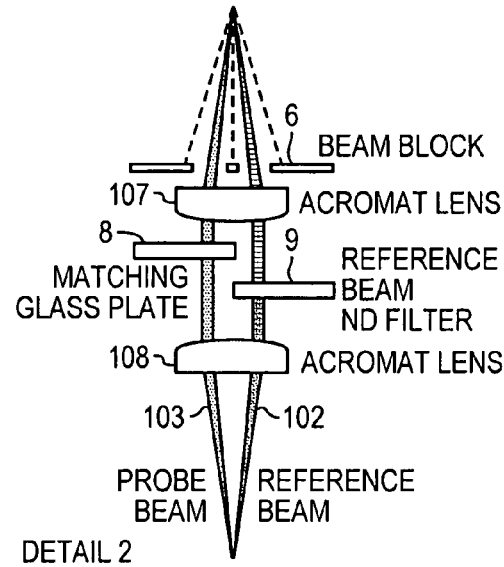
FIG. 3B shows a second detail expansion from FIG. 2.
Figure 3C:
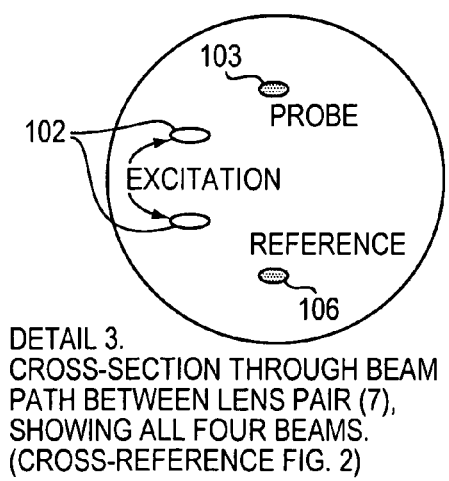
FIG. 3C shows a third detail expansion from FIG. 2.

FIG. 3B relates to the arrow marked Detail 2 in FIG. 2. The probe and reference beams 103, 102 pass through the beam block 6 and through the first achromatic doublet lens 107. The reference beam 102 passes through the ND filter 9, while the probe beam 103 passes through the matching glass plate 8. Both beams then pass through achromatic doublet 7. In FIG. 2, elements 8 & 9 appear to be in the same pathway, because of the angle of view. If viewed from another side, they are not, as shown in FIG. 3B. FIG. 3C relates to the arrow marked Detail 3 from FIG. 2. It is a cross section through the beam path between the lens pair 107,108, showing all four beams.

Figure 3D:
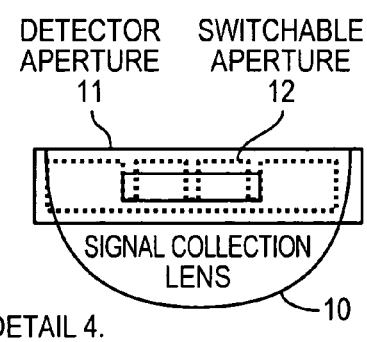
FIG. 3D shows a fourth detail expansion from FIG. 2.

FIG. 3D relates to the arrow marked Detail 4 in FIG. 2. Through the lens 10, reflected beam 205 then passes through detector aperture 11 and switchable aperture 12. The lens 10 is not fully circular, because it is cut off to accommodate the vision zoom lens assembly 202.

Details of the optical layout are described more fully in the sections below.

4. Lasers

4.1 Excitation Laser

The excitation laser 207 is a diode-pumped, passively Q-switched, frequency-doubled Nd:YAG laser with "microchip" design supplied by JDS Uniphase (product name NG-00320-TH1).

The laser has wavelength of 532 nm, pulse energy typically 4 µJ (spec.>3 µJ), pulse duration ~0.5 ns (spec.<0.7 ns), repetition rate 1500 Hz, and $TEM_{00}$ spatial mode. The excitation beam is linearly polarized at ~25° with respect to the base plane.

The output beam is not collimated but rather is converging with beam waist of Gaussian radius 45 µm (1/e) being located at 200 mm from the laser front panel. These parameters were calculated by us based on the requirement of placing the beam waist at the sample, as outlined in Section 6.0.

The laser assembly contains a built-in photodiode that provides an output signal used to trigger data acquisition by the oscilloscope.

4.2 Probe Laser

The probe laser 208 is a GaAlAs laser diode (SDL-5431-G1) manufactured by JDS Uniphase, with product name SDL-5431-G1.

The laser has wavelength 830 nm, power ~200 mW, and $TEM_{00}$ operation. The laser beam is elliptical (long to short axis ratio ~3:1) and polarized along the short axis. Note that the polarization of both probe 208 and excitation lasers 207 is in general insignificant for most think film and solid surface applications, although there is a minor effect of polarization on the performance of some optics such as dichroic mirror (FIG. 2, item 4).

Figure 4A:
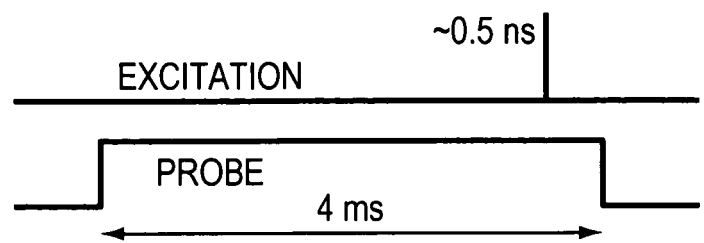
FIG. 4A shows a sketch of the excitation and probe laser light intensity output vs. time.

Although the laser diode could operate continuously, it is modulated by a square wave with duty cycle ~30% in order to decrease the thermal load and increase the lifetime. Only a 100 ns long segment of the probe laser pulse per each excitation pulse is used to acquire the signal. In practice, however, a much longer probe pulse is required. One reason is that during the signal acquisition, the probe intensity should stay flat. Also, due to the 1 MHz low-frequency cut-off of the detector, the leading edge of the probe pulse generates a long-lasting transient in the signal. Therefore, the excitation pulse should be far from the edges of the probe pulse, especially from its leading edge. FIG. 4A shows a sketch of the excitation and probe laser light intensity output vs. time.

5.0 Phase Mask

5.1 Binary (Single-etch) Phase Mask

5.1.1. Binary Phase Mask Description

Figure 5:
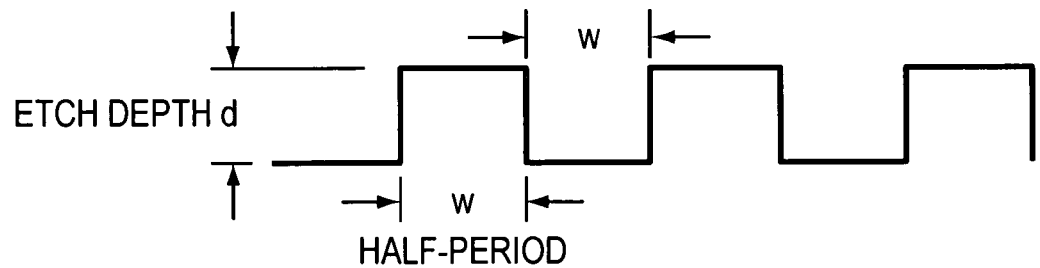
FIG. 5 shows the etch profile of a binary (single-etch) phase mask

The binary phase mask is made of fused silica FIG. 5 shows the phase mask etch profile. The mask typically contains 15 phase mask patterns, each of size typically 2×3 mm, manufactured on the same substrate. The phase mask half-period w (in µm) typically ranges from 3 to 15 microns.

FIG. 5 schematically shows one of the patterns. Different patterns have different half-width w but the same etch depth. The etch depth for all patterns is 1833 nm+/−3%. (See the explanation in Section 5.3, below.) The back side of the phase mask is coated by a broadband antireflection coating.

5.1.2 Diffraction Efficiency of a Binary Phase Mask

Under the assumptions that the phase mask period is much larger than the optical wavelength, the etch depth is small compared to the period, and the etch depth is small compared to the optical wavelength, the diffraction efficiency of a phase mask with a square profile is given by equation (3) of FIG. 11D, where N is the diffraction order, d the etch depth, n the refractive index, $\lambda$ is the optical wavelength, $I_0$ is the optical intensity of the beam incident on the phase mask and $I_N$ is the optical intensity in the N-th diffraction order. The "+" branch should be used for zero-order and "−" for odd orders. All even orders (except the $0^{th}$) are absent.

Using Eq. (3), at an etch depth corresponding to an optical path difference of $1\lambda$, i.e. $d(n-1)=0, \lambda, 2\lambda, \ldots$ the intensity of the zero order is 100% and all other diffraction orders are absent. At an etch depth with path difference equivalent to $\lambda/2$, the zero order is absent and the intensity of odd orders is maximized, with the maximum intensity of an N-th diffraction order $I_{oddNmax}$ given by the equation of FIG. 11E. For the first order, the maximum intensity is $4/\pi^2=40.5\%$, i.e. the maximum diffraction efficiency in both (±1) orders is 81%.

In reality, even orders are not completely absent as predicted by the simple theory used for Eq. (3), because the assumptions justifying the equation are not completely valid, e.g. the etch depth is not very small compared to the phase mask period. The presence of non-zero intensity in the even orders is fortunate, because the $2^{nd}$-order diffraction of the probe laser is used to create the heterodyne reference beam. The intensity of even orders increases with the etch depth and also increases (nearly quadratically) with the wavevector, equal to $2\pi/\Lambda$. Unlike zero and odd orders, even orders do not vanish at a particular etch depth.

5.1.3 Phase Mask Etch Depth

In choosing the etch depth of the phase mask, we considered the following requirements:

1. The (±1) diffraction orders of the excitation laser ($\lambda_e$=532 nm) should be maximized.
2. The zero-order of the probe laser ($\lambda_p$=830 nm) should be maximized.
3. There should be weak (but stable) 2nd order diffraction of the probe (830 nm) for the reference beam.

Fortunately, requirements 1 and 2 were easy to meet simultaneously because an optical path difference of $1\lambda_p$ corresponds to approximately $\frac{3}{2} \lambda_e$. It was decided to optimize the phase mask for 830 nm, making the etch depth equivalent to exactly $1\lambda_p$. The deviation of the probe beam incidence angle from 90° was disregarded as a small effect. The refractive index of fused silica at 830 nm is 1.4528. Therefore, the etch depth d was calculated in accordance with equation (4) of FIG. 11F. This choice resulted in all three requirements being adequately satisfied, as shown below.

5.1.4 Calculated and Measured Phase Mask Efficiency

The table of FIG. 11G lists the diffraction efficiencies calculated using Eq. (3) with etch depth of 1833 nm. The calculations used refractive index n=1.4607 at 532 nm and n=1.4528 at 830 nm. The expected worst-case effects of a 3% error in the etch depth are as shown in the table of FIG. 11H.

Experimental measurements generally agree with the numbers in the table above. However, the zero-order intensity at 830 nm is observed to be smaller than expected, varying between ~90% at half-period 9 μm and ~80% at 4 μm. The reason is the presence of even diffraction orders that are not accounted for by the simple theory of Eq. (3). As mentioned above, the intensity of even orders increases as the phase mask period shrinks. For example, the $2^{nd}$-order diffraction used as a reference beam varies between ~0.5% at half-period 9 μm and ~2% at 4 μm.

5.2 Dual-Etch Phase Mask

As pointed out above, one disadvantage of a binary phase mask design is the dependence of the reference beam intensity (obtained from the second-order diffraction) on the phase mask period. The dependence is nearly quadratic which results in undesirably large variations in the reference beam intensity for a wide SAW wavelength range e.g. 1-10 μm. To improve the stability of the second order diffraction over a wide range of periods, the phase mask can be modified in accordance with FIG. 14A or B, using a dual-etch design.

The dual etch design improves performance of a binary phase mask by means of:

(1) overlaying an additional (secondary) line pattern on top of the existing (primary) binary phase mask ("EM") pattern, the former having the same orientation and twice the spatial frequency as the latter;
(2) optimizing the following parameters of resulting grating profile: e1 (etch depth of the primary grating), e2 (etch depth of the secondary grating); w (secondary grating feature width) and δ (offset between the two gratings).

FIG. 14A shows an embodiment of the dual etch design in which the secondary pattern was superimposed positively, i.e. sticking up. FIG. 14B shows an embodiment of the dual etch design in which the secondary pattern was superimposed negatively, i.e. as depressions in the primary pattern.

The optimization of parameters was performed using standard software for diffraction grating analysis. The proposed design phase masks are preferably manufactured with required precision by dual-step lithography and etch process using modern equipment.

Figures 15, 16:
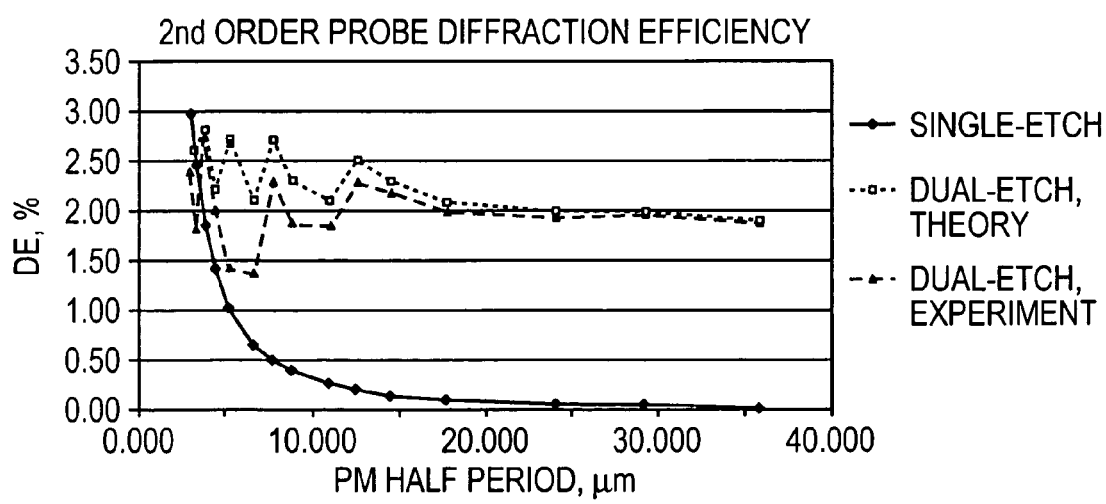
FIG. 15 shows parameters of a dual-etch phase mask used in one of the embodiments.
FIG. 16 shows reference beam intensity vs. phase mask period for the binary (single-etch) phase mask and for the dual-etch phase made to the specifications listed in FIG. 15.

FIG. 15 presents values of e1, e2 and w used in one embodiment of the phase mask. Preferably all of these patterns would appear on a single substrate, and the substrate would appear on a motorized stage so the system could move from pattern to another.

FIG. 16 shows the dependence of the reference beam intensity on the phase mask period for the binary phase mask described earlier vs. the dual-etch phase mask. In this figure, the units on the vertical axis are diffraction efficiency of the second order of diffraction measured in percent and the units on the horizontal axis are phase mask half period in microns. The graph with the diamond shaped points shows the results with a single etch design. The graph with the square shaped points shows the theoretical results with a dual etch design. The graph with the triangularly shaped points shows the experimental results with a dual etch design. One can see that the use of a dual-etch phase significantly decreases variations in the reference beam intensity as a function of phase mask half period.

5.3 Phase Mask Dithering

The phase mask is mounted on a computer-controlled motorized stage used to switch from one phase mask pattern to another. Another function of the phase mask motor is to perform phase mask dithering, i.e. periodic motion, typically within a range of +/−0.5 mm from the nominal position, as the signal is averaged. This is done in order to randomize the phase of the laser-induced grating on the sample with respect to the surface roughness profile. As a result, the relative phase of the signal and any light scattered from the surface roughness is also randomized and the contribution due to their coherent interference in the averaged signal is suppressed. More information relating to phase mask dithering may be found in U.S. Pat. No. 6,188,478.

6.0 Excitation Beam Optics

The excitation beam 102 first passes through a motor-controlled stepped ND filter 1 that attenuates the beam.

The beam then passes through a cylindrical lens (f=40 mm) 2 and through a dichroic mirror 4 optimized to transmit at 532 nm and reflect 830 nm at a 45° angle. After passing through the mirror, the beam impinges on the phase mask 5 at normal incidence.

The spot size at the phase mask is such that the nominal spot size at the sample will be 300×50 μm. The spot sizes at the phase mask and at the sample are not identical because of the incidence angle of the beam upon the sample. The spot size is controlled by both the output optics of the laser and by the cylindrical lens. The position of the lens, see table in FIG. 11C, is calculated, given the parameters of the Gaussian beam output of the laser, in order to minimize the short axis of the spot at the phase mask.

Figure 9:
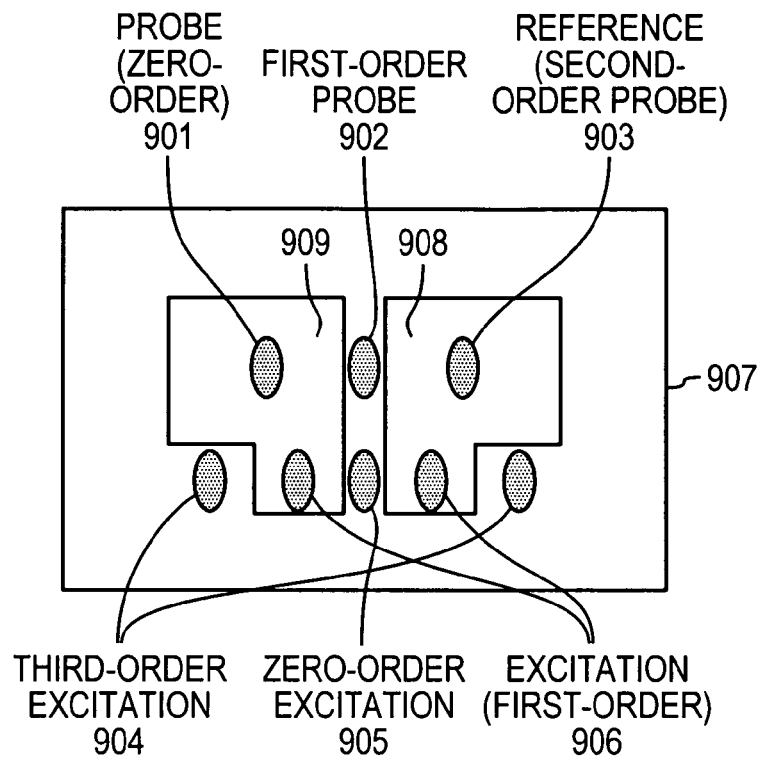
FIG. 9 shows the geometry of the beam blocking devices.

After the phase mask, the excitation beams pass through a beam block 6 that cuts off zero, third, and higher diffraction orders. The beam block 6 used in one of the embodiments is shown in more detail in FIG. 9 and includes a piece of metal 907 shaped to block the beams that should be blocked and with holes 908 and 909 allowing the needed beams through. The figure shows the following beams passing through the holes 908 and 909:

the zero order 901 probe beam;
the reference beam 903, which is also the second order probe beam; and
the first orders 906 of the excitation beam.

The figure shows the following beams being blocked by the metal piece 907:
the first order 902 of the probe;
the zero order 905 of the excitation beam; and
the third order 904 of the excitation beam.

Higher-order beams also blocked by the beam block, are not shown. The beam block shown in FIG. 9 can be used for the range of SAW wavelength Λ less than 1:3 e.g. 4-10 µm. To achieve a wide range, a more complicated "comb-like" design or, alternatively, adjustable beam blocks mounted on a motorized stage should be used.

After passing through beam blocking element 6, the remaining beam portions pass through a system of two achromatic doublet lenses 7, 107, 108, that image the phase mask onto the sample surface. Aberration-related requirements on the imaging system are considered in Section 7.0.

It is desirable to make the magnification, which controls the period of the interference pattern at the sample, as insensitive as possible to small deviations of the vertical position of the sample surface. By Gaussian beam analysis, it can be shown that the interference pattern period will be independent of δz—the distance of the sample surface from the image plane—to first order of δz if the excitation beam waist along the long dimension of the spot is placed at the sample. In order to achieve it, the input parameters of the excitation beam at the input of the optical system are preferably modified making the excitation beam convergent rather than collimated.

A ray-tracing analysis was performed to determine what should be the input parameters of the Gaussian beam in order to place the waist at the sample surface. This analysis resulted in the excitation laser Gaussian beam specs listed in Section 4.1. This arrangement reduced the dependence of the measured frequency on δz to typically <0.05 MHz per 20 µm.

Optionally, a 3 mm-thick plane-parallel glass plate can be inserted in the excitation beam path at an angle of 16° (item 14 in FIG. 2). This plate shifts the laser spot along its long dimension by about 300 µm, such that the probe spot becomes located outside the excitation area. This arrangement may be beneficial for some applications requiring enhanced accuracy of the frequency measurements because the signal in this case consists only of acoustic oscillations and is not affected by the thermal grating, please see A. A. Maznev, et al., "Optical Heterodyne Detection of Laser-Induced Gratings," Opt. Lett. 23, 1319 (1998).

7.0 Probe Beam Optics

The probe laser beam 103 first passes through a system consisting of a retroreflector 301 and a mirror 302, as shown in FIG. 3A, Detail 1. This system is used for motorized control of the beam displacement from the axis of the focusing lens. After the focusing lens, this displacement will translate into a variation in the beam angle while the focal spot position at the phase mask stays unchanged. Section 8 considers the probe beam angle control in more detail.

Figure 6:
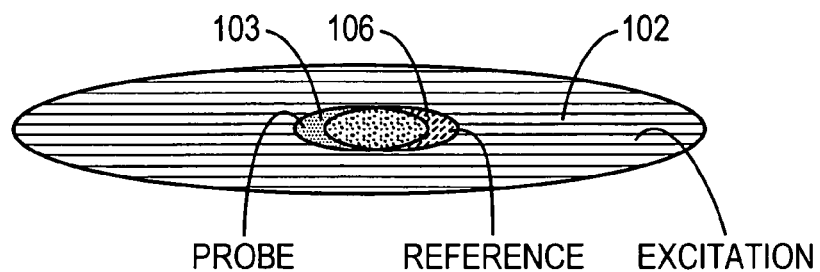
FIG. 6 shows laser spots at the sample surface.

After the retroreflector/mirror system 301/302, the beam 103 passes through the focusing lens 3 (f=80 mm) and is reflected by a dichroic mirror 4 to be overlapped with the excitation beam 102 at the phase mask 5. The probe beam spot size is 50×25 µm with the long axis parallel to the long axis of the excitation beam, see FIG. 6, which shows the spot size of the probe 103, excitation 102, and the reference 106 beams at the sample surface 109.

The lens system imaging probe and excitation spots on the sample consists of two lens assemblies, typically achromatic doublets 107, 108 with focal distance 80 mm. The parameters of the achromatic doublets are optimized in order to meet the following requirements as far as aberrations are concerned:

1. Spherical aberration at 830 nm should be small enough so that a good overlap of the probe and reference beam at the sample surface (fixed in space) is preserved as the angle between the beams varies. Overlap of the two excitation beams is much less critical because the excitation spot is larger while the angle between the beams is smaller.
2. Spherical plus chromatic aberrations should be small enough that the excitation/probe beam overlap is preserved.

The space between the two lenses 107, 108 is used for the ND filter 9 attenuating the reference beam 106. The ND filter 9 is also used to control the reference beam phase. The filter is preferably highly parallel (see below). The probe beam 103 passes through a matching glass plate 8, which preserves the temporal coherence between the two beams. The phase control plate 9 is for the reference beam 106 and the matching plate 8 is for the probe beam 103. The heterodyne phase is optimized during the system set-up by adjusting the ND filter angle, which changes the optical path length. The phase change introduced by the filter should be the same for all phase mask periods. Since the location of the reference beam on the filter varies, this means that this component should have very tight specifications for flatness and parallelism (1 arc sec), and the same is true for the matching plate in the probe beam path.

The optical density of the ND filter 9 determining the reference beam intensity is equal to 1.7. Taking into account the diffraction efficiency of the phase mask and the additional attenuation by the ND filter, the reference beam intensity is a factor of about $10^4$ smaller than the probe intensity. The reference beam intensity also depends on the phase mask period, as discussed in Section 5.0.

The chosen reference beam intensity level is the result of a compromise. Increasing it would better help suppress the effect of parasitically scattered light and thus yield better measurements on "difficult" samples, such as very rough electroplated copper ("ECD") or very small test pads where a lot of probe light scatters from the edges of the pads. On the other hand, this would increase the effect of fluctuations of the probe laser intensity, and also might result in detector saturation. In the preferred embodiment, the latter factor was taken as limiting the intensity of the reference beam.

Figure 7A:
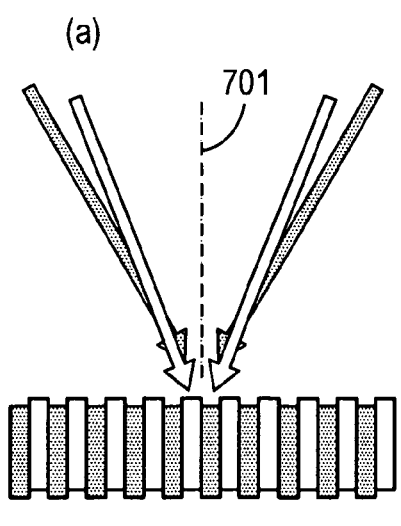
FIG. 7A shows a "symmetric" configuration, where heterodyne phase will be independent of the distance z of the sample surface from the image plane.
Figure 7B:
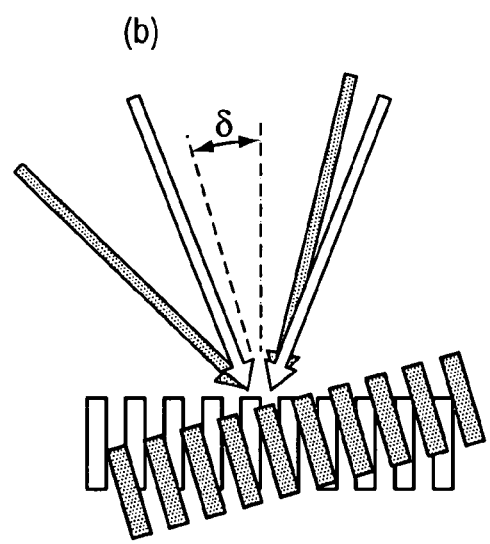
FIG. 7B shows the more general case, where heterodyne phase will depend on z.

8.0 Probe Beam Angle Control 8.1 Heterodyne Phase and Z Dependence of Signal Intensity FIG. 7A shows a "symmetric" configuration, where heterodyne phase will be independent of the distance z of the sample surface from the image plane. FIG. 7B shows the more general case, where heterodyne phase will depend on z.

As described above the phase is optimized by adjusting the angle of the ND filter 9 in the reference beam path.

Exactly in the image plane, the phase will be the same for all phase masks. If one moves out of the image plane, the phase will stay unchanged only if the excitation and probe/reference beam pairs have the same bisector line 701, as illustrated in FIG. 7A. As described in Section 2.0, there is a small angle between the planes formed by the excitation and probe/reference beam pairs, therefore, in order to be strictly correct, one could replace the word "bisectors" in section 2.0 with the phrase "projections of the bisectors on the plane of the drawing in FIG. 7".

If the beam pairs do not have the same bisector line, as shown in FIG. 7B, the interference patterns formed by the two beam pairs will be at an angle with respect to each other, which will cause the spatial phase difference between them to depend on the z-position. In this case, the dependence of the heterodyne phase on the distance z of the sample surface from the image plane is given by equation (5) of FIG. 11I, where q is the grating wavevector and $\delta$ is the angle between the bisector of the probe/reference beam pair when projected
onto the plane formed by the excitation beams; and
the bisector of the excitation beam pair.

Figure 8:
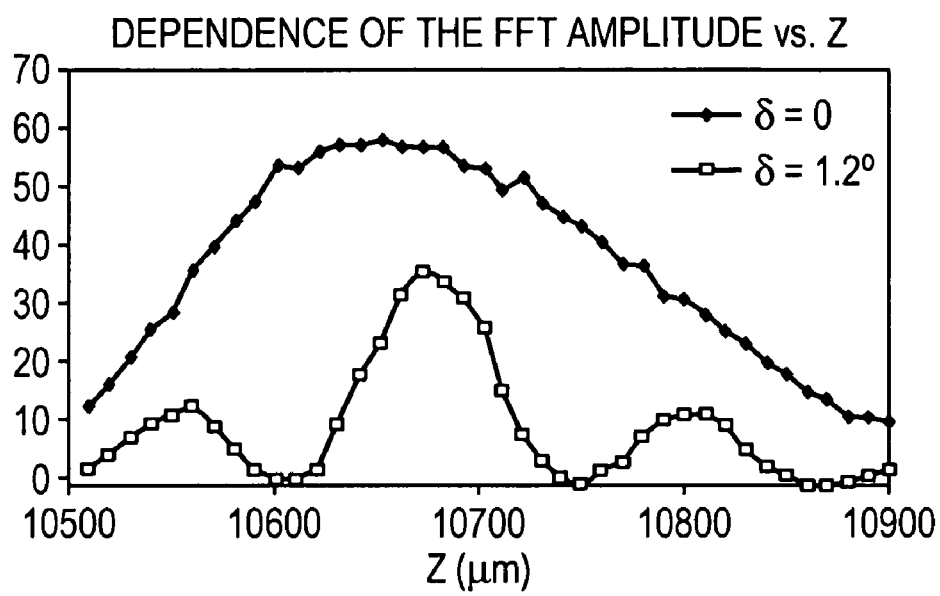
FIG. 8 is a graph, which shows the z-dependence of the FFT amplitude for zero and non-zero values of δ.

Consequently, the dependence of the signal amplitude on z will undergo oscillations with a period $\Lambda/\tan(\delta)$, where $\Lambda=2\pi/q$ is the grating wavelength. For certain values of the heterodyne phase, the signal amplitude will be positive, while for others it will be negative. Since the amplitude of the peak in the FFT power spectrum of the detected signal is quadratic with respect to the signal, the period seen in the autofocus curve, which is a plot of FFT power versus z position, will be two times smaller, per equation (6) of FIG. 11J. This periodicity is illustrated in FIG. 8, which shows the z-dependence of the FFT amplitude for zero and non-zero values of $\delta$. FIG. 8 shows a plot of FFT power measured in any arbitrary units as a function of z, measured in microns. The graph with the diamond shaped points corresponds to a value of $\delta=0$, while the graph with the square points corresponds to a value of $\delta=1.2°$. The amplitude undergoes oscillations if is $\delta$ non-zero.

For measurements, one would like to always keep $\delta=0$ in order to minimize the dependence of the measured signal on the z-position of the sample surface. However, the reference beam angle depends on the wavevector, while the probe beam angle does not. (This is due to the fact that the probe beam corresponds to zero-order diffraction by the phase mask while the reference beam is produced by 2nd-order diffraction.) Consequently, for fixed incidence angle of the probe beam upon the phase mask, if $\delta=0$ for any given wavevector, it will become non-zero if the phase mask period is changed by moving to a different phase mask pattern. As discussed above, a number of phase mask patterns with different periods are fabricated on a single substrate. Therefore, an additional moving element (the retroreflector, below referred to as RR) is needed to adjust the probe beam angle for each phase mask period in order to keep $\delta=0$. This results in broad FFT-power vs. z curves, with Full Width at Half Max ("FWHM") of about 300 μm.

Figure 10:
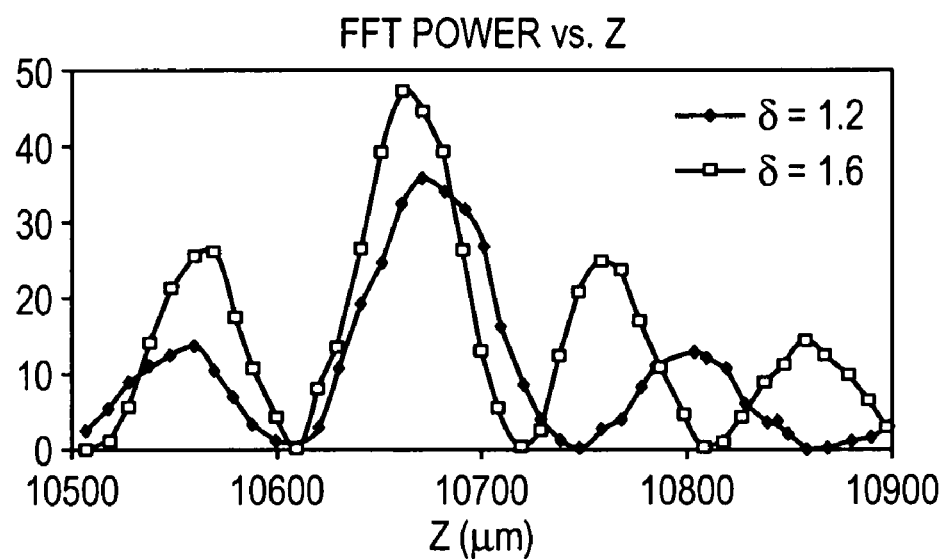
FIG. 10 is a graph showing FFT-power vs. z for two values of δ.

While a broad FFT-power vs. z curve, such as occurs with $\delta=0$ is desirable for measurements, it is undesirable for auto focusing. For autofocus purposes, one would prefer to have a rather sharp dependence of FFT power on z, so that the focus position may be precisely located. In the earlier versions of the optical system, see Refs. A, R & T, above, this was achieved by using a 3-beam phase mask for autofocus. However, this phase mask cannot be used in a heterodyne setup. Therefore, it is preferred use a special phase mask/ retroreflector combination with non-zero $\delta$ as the autofocus configuration, thereby achieving a narrow FFT-power vs. z curve. This is discussed further below with respect to FIG. 10.

8.2 Retroreflector

FIG. 3A presents a simplified schematic of the probe beam optics before the phase mask. The goal of the design is to change the angle of the probe beam 103 at the sample without changing the probe spot position at the sample. As the retroreflector (RR) motor moves, the probe beam is shifted by twice the RR motor motion distance. This RR/mirror combination is preferred over a single mirror because the retroreflector 301 preserves a constant angle of the reflected beam (parallel to the incident beam) even if the RR angle undergoes slight variations as the stage 301 moves. After the focusing lens 3, the displacement of the beam 103 from the lens axis is translated into a change in beam angle while the position of the beam 103 in the focal plane remains unchanged. The preferred focusing lens 3 has a focal length f=80 mm.

The RR motor position for each phase mask is determined by the requirement that $\delta=0$. The incidence angle $\theta/2$ of the probe beam is then given by equation (7) of FIG. 11K, where $\lambda$ is the probe beam wavelength (i.e. 830 nm). Consequently, the motor position is given by equation (8) of FIG. 11L, where f is the focal distance of the probe focusing lens and $X_0$ is a constant offset. The offset needs to be determined experimentally for each system.

8.3 Autofocus

Autofocusing means automated positioning the sample surface at the correct height (i.e. at the imaging plane of the optical system). For autofocusing (AF), it is preferred to use a PM/RR motor position combination with non-zero $\delta$ resulting in a narrow, autofocus peak. This provides a unique definition of the focus plane by allowing one to distinguish between the "true" central peak of the AF curve and side maxima. See FIG. 10, which is similar to FIG. 8 except it shows $\delta=1.2°$ and $\delta=1.6°$. When $\delta$ is decreased (by varying the RR position), the true central peak stays in place steadily turning into a single broad maximum (such as the one in FIG. 8), while the side maxima move away.

Although the exact value of $\delta$ is not important for autofocusing, the autofocus configuration should be made compatible with a switchable aperture, so that the aperture can be engaged during autofocus. The system is preferably configured in such a way that autofocusing is performed with $\Lambda=6$ μm, but that the autofocus signal beams are transmitted through the switchable aperture slot corresponding to $\Lambda=10$ μm. In this case, the value of $\delta$ is given by equation (9) of FIG. 11M, which yields $\delta\sim1.6°$. The probe beam angle in this configuration is given by equation (10) of FIG. 11N and the corresponding RR motor position is determined using Eq. (8).

9.0 Signal Beam Optics and High-Speed Detector

This section gives more discussion of Detail 4 of FIG. 3D and the signal beam optics 204 in FIG. 2. The signal 205, i.e. SAW-diffracted probe and reflected reference beams, are focused onto the detector by the signal collection lens 10 (see FIG. 2.) This lens 10, an achromatic doublet with focal distance 50 mm, images the probe spot at the sample surface 109 onto the detector 206. Therefore, the location of the signal spot on the detector 206 stays the same even as the direction of the signal beam varies depending on the phase mask period. Part of the lens 10 is cut off to free space for the vision system assembly 201.

After the lens, the signal beams pass through the detector apertures, items 11 and 12 in FIG. 2. The first aperture 11 blocks the directly reflected probe beam and reduces the amount of scattered light passing to the detector. The second aperture 12, which is switchable and moves into place under computer control, further reduces the amount of scattered light. This switchable aperture 12 contains 3 slots, which transmit the signal beams for SAW wavelengths 4, 6, and 10 μm, respectively. The 3 separate slots are necessary because the position of the signal beam at the aperture varies with the phase mask period. Detail 4 in FIG. 3 shows a view along the beam path when the switchable aperture is engaged. In another embodiment, instead of the switchable aperture with several slits, a single-slit aperture is used, mounted on a motorized stage, which places the aperture at the optimal position for each phase mask period.

Finally, the signal 205 passes through a colored glass filter 13 in front of the detector 206 that cuts off scattered excitation light.

The high-speed detector (Hamamatsu C5658-SPL-LG) is a customized version of Hamamatsu's standard avalanche photodiode/preamplifier module C5658. The customization was needed because the overload threshold of the preamplifier was too low for use in a heterodyne system, which has a higher signal level compared to the non-heterodyned system.

Experimental Results

Figure 12A:
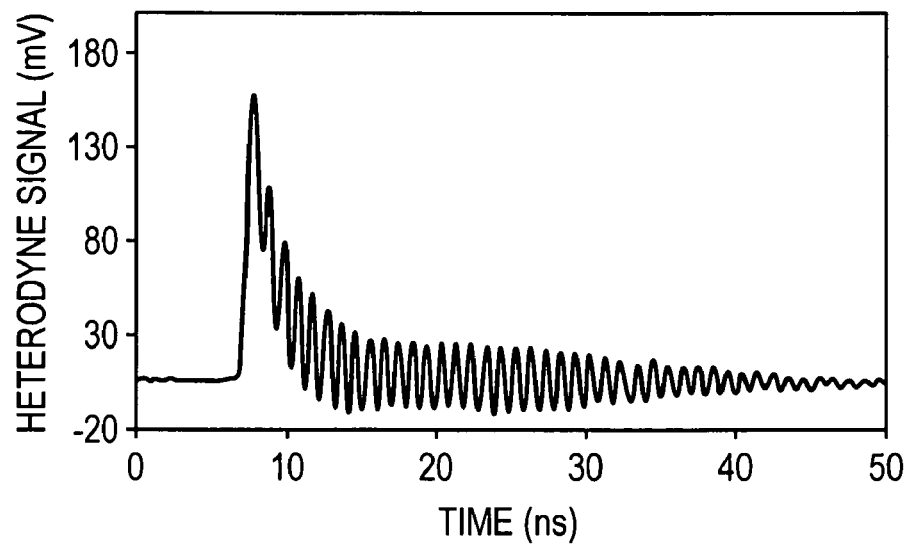
FIG. 12A shows the signal from a 4000 Å-thick 50×100 μm copper pad fabricated on a silicon wafer. The signal is obtained with the apparatus of the preferred embodiment at an SAW wavelength of 2 μm.
Figure 12B:
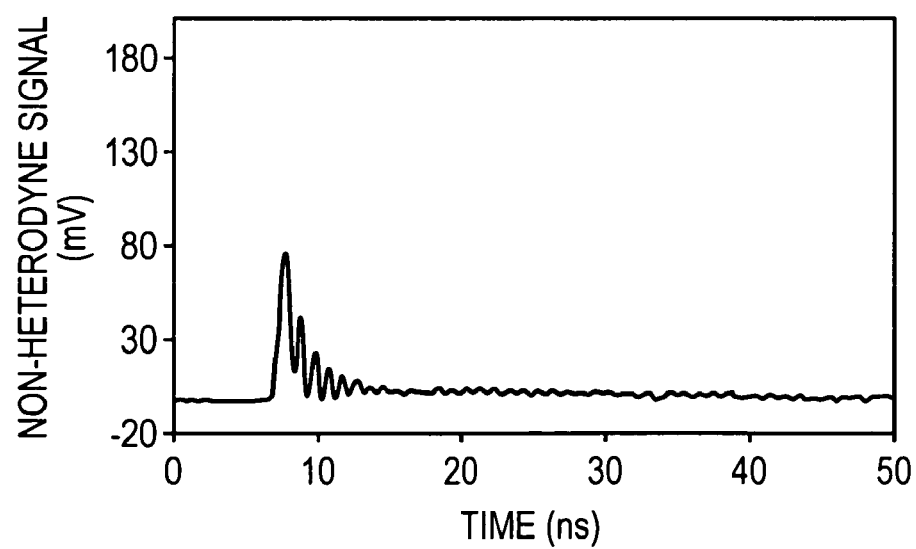
FIG. 12B show the signal from the same sample as in FIG. 12A obtained without optical heterodyning (i.e. with the reference beam blocked).

FIGS. 12A & B show signal waveforms plotted with milivolts on the vertical axis and nanoseconds (ns) on the horizontal axis. The curve of FIG. 12A was obtained with heterodyning and the curve of FIG. 12B was obtained without heterodyning. Both curves were taken from the same sample, i.e. 50×100 μm copper test pad fabricated on a silicon wafer. One can see that the heterodyne signal is not only higher in amplitude, but is also more regular, with a much larger number of acoustic oscillations present. The latter advantage is a consequence of the fact that the heterodyne signal is linear with respect to the displacement amplitude of the sample surface.

Another advantage of a heterodyne apparatus is relative suppression of parasitic heterodyning caused by scattering of probe light off surface roughness and edges of structures on finely patterned wafers. As a result, heterodyne system yields higher repeatability of the acoustic frequency measurements, and, consequently, of the measurements of film thickness and/or properties.

FIG. 13 presents experimentally determined thickness measurement repeatability on different structures obtained with the heterodyne system vs. a prior art system (described in Refs. A & R-T, above). The data show standard deviations determined from typically more that 100 independent measurements on each structure. Measured sample/structures were:

4000 Å-thick Cu, 50×100 μm test pad;
4000 Å-thick Cu, 50×50 μm test pad;
4000 Å-thick Cu damascene array (0.5 μm lines separated by 0.5 μm SiO2) in a 50×100 μm test pad;
12000 Å electroplated Cu film with rough surface, blanket wafer; and
225 Å-thick Ta, blanket wafer.

As can be seen from the data, the more dramatic improvements are found in samples with finely patterned structures. The greatest improvement was seen in the damascene line array.

Optical heterodyning results in a 3 to 30-fold improvement in the repeatability.

From reading the present disclosure, other modifications will be apparent to persons skilled in the art. Such modifications may involve other features which are already known in the design, manufacture and use of opto-acoustic measurement devices and which may be used instead of or in addition to features already described herein. Such modifications could also include changes in the dimensions of optical components, changes in the distances or angles between components, and replacement of any of the components by alternative ones in order to improve the function of the apparatus. Although claims have been formulated in this application to particular combinations of features, it should be understood that the scope of the disclosure of the present application also includes any novel feature or novel combination of features disclosed herein either explicitly or implicitly or any generalization thereof, whether or not it mitigates any or all of the same technical problems as does the present invention. The applicants hereby give notice that new claims may be formulated to such features during the prosecution of the present application or any further application derived therefrom.

The word "comprising", "comprise", or "comprises" as used herein should not be viewed as excluding additional elements. The singular article "a" or "an" as used herein should not be viewed as excluding a plurality of elements.

The invention claimed is:

1. A measurement device comprising:
a probe beam source configured to supply a probe beam;
an excitation beam source configured to supply an excitation beam;
a diffractive element configured to split the probe beam into a probe/reference beam pair comprising a probe beam portion and a reference beam portion, and configured to split the excitation beam into two excitation beam portions, wherein most of the probe beam is transmitted into the zero diffraction order;
optics configured to overlap the two excitation beam portions on a sample surface and configured to overlap the probe beam portion and the reference beam portion on the sample surface, wherein the probe beam portion is diffracted by material disturbances produced by the excitation beams; and
a detector configured to monitor coherent interference of a diffracted part of the probe beam portion with the reference beam portion.

2. The device of claim 1, wherein the diffracted part of the probe beam portion is collinear with the reference beam portion.

3. The device of claim 1, wherein a heterodyne signal incident off the sample surface satisfies the equation $$I_S = I_D + I_R + 2\sqrt{I_D I_R} \cos\phi$$

where $I_D$ is a signal diffracted off sample surface, $I_R$ is the second reference beam portion, $I_S$ is the optical intensity at a detector a result of the coherent interference of the diffracted signal and reference beam, and $\phi$ is the phase difference between the diffracted part of the probe beams portion and the reference beam portion.

4. The device of claim 1, wherein the diffractive element comprises a phase mask configured to split the excitation beam simultaneously with the probe beam.

5. The device of claim 4, wherein the phase mask is configured to diffract most of the excitation beam into the +/−1 diffraction orders and configured to diffract most of the probe beam into the zero diffraction order so that the probe beam portion is the zero order diffraction of the probe beam and the reference beam portion is the second order diffraction of the probe beam.

6. The device of claim 5, wherein the optics configured to overlap the beam portions on the sample surface are configured to place the Gaussian waist of the excitation beam at the sample surface.

7. The device of claim 5, wherein the phase mask etch depth is approximately equal to the wavelength of the probe beam divided by n−1, where n is the refractive index of the phase mask material.

8. The device of claim 5, wherein the phase mask etch depth is approximately equal to 1.5 times the wavelength of the excitation beam divided by n−1, where n is the refractive index of the phase mask material.

9. The device of claim 5, wherein the phase mask is fabricated by overlaying a secondary line pattern on top of a primary binary phase mask pattern, the secondary line pattern having the same orientation and twice the spatial frequency as the primary binary phase mask pattern.

10. The device of claim 5, further comprising optics for blocking the zero diffraction order and third and higher diffraction orders of the excitation beam.

11. The device of claim 4, wherein the bisector of the probe/reference beam pair projected onto the plane formed by the excitation beams makes an angle of zero with the bisector of the excitation beam pair.

12. The device of claim 4, wherein the probe/reference beam pair is contained in a different plane from the excitation beam pair.

13. The device of claim 4, wherein the phase mask is a phase grating.

14. The device of claim 1, wherein the excitation beam supplied by the excitation beam source is not collimated but is characterized by Gaussian beam parameters selected such that the Gaussian beam waist is located at the sample surface.

15. The device of claim 1, comprising a displacement plate configured to shift the excitation beam such that the probe spot becomes located outside of the excitation area.

16. The device of claim 1, wherein spot sizes of the probe beam portion and the reference beam portion are smaller than a test pad on the sample surface.

17. The device of claim 1, comprising an attenuating filter in the path of the second reference beam portion and a matching glass plate in the path of the probe beam portion, wherein both the attenuating filter and the matching glass plate have surfaces parallel to about 1 arc second in order to introduce the same phase shift independently on positions of both the probe beam portion and the reference beam portion, and wherein at least one of the attenuating filter and the matching glass plate is adjustable in angle in order to optimize the heterodyne phase.

18. The device of claim 1, wherein the optics configured to overlap the beam portions on the sample surface comprises at least one lens assembly optimized to minimize aberrations at both probe and excitation wavelengths.

19. The device of claim 18, wherein at least one of the lens assemblies is an achromatic doublet.

20. The device of claim 1, further comprising a vision system configured to capture an image of the sample surface, wherein the vision system defines an optical axis that is approximately perpendicular to the sample surface.

21. The device of claim 20, wherein an angle between an optical axis of the vision system and the probe/reference beam bisector is about 16°, wherein the optics configured to overlap beam portions on the sample surface comprises a lens assembly in which the lenses located next to the vision system are cut off to achieve the angle of about 16°, and wherein an angle between planes containing the excitation and probe/reference beam pairs is about 3.5°.

22. The device of claim 20, wherein the vision system comprises a camera.

23. The device of claim 22, wherein the camera is positioned such that incident excitation and probe/reference beams are situated on one side of the camera and beams from the sample to the detector are situated on the other side of the camera.

24. The device of claim 23, wherein the angle between the camera and the probe/reference beams is reduced by cutting an unused part of at least one lens assembly of the optics configured to overlap beam portions on the sample surface.

25. The device of claim 1, further comprising a retroreflector mounted on a motorized stage between the probe beam source and the diffractive element.

26. The device of claim 25 further comprising a flat mirror and a focusing lens.

27. The device of claim 25, wherein the diffractive element comprises a phase mask, and wherein the retroreflector is positioned by the motorized stage to achieve, for a given period of a pattern on the phase mask, an angle of zero between the projection of the bisector of the probe/reference beam pair onto the plane formed by the excitation beam pair and the bisector of the excitation beam.

28. The device of claim 25, wherein the retroreflector is configured to vary an incident angle of the probe beam on the diffraction element without changing a probe spot location on the sample surface.

29. The device of claim 1, further comprising a switchable aperture between the sample and the detector, wherein the aperture has one or more slots for transmitting the signal to the detector, each corresponding to a specific phase mask period.

30. The device of claim 29, wherein the aperture mounted on a motorized stage is placed between the sample and the detector, and wherein the position of the said aperture is optimized for each phase mask period.

31. The device of claim 1, wherein the sample has a finely patterned structure fabricated at its surface.

32. The device of claim 1, wherein the sample is a damascene line array.

33. The device of claim 1, further comprising an analyzer configured to measure at least one property of the sample by analyzing a signal from the detector.

34. The device of claim 1, wherein the sample comprises at least one member of the group consisting of a thin film, a thin film structure, and a solid surface.

35. A method for measuring one or more properties of a thin film, thin film structure, or solid surface, the method comprising:
  supplying a probe beam;
  supplying an excitation beam;
  splitting the probe beam into a probe/reference beam pair comprising a probe beam portion and a reference beam portion, wherein most of the probe beam is transmitted into the zero diffraction order;
  splitting the excitation beam into two excitation beam portions;
  overlapping the two excitation beam portions on the thin film, thin film structure, or solid surface;
  overlapping the probe beam portion and the reference beam portion on the thin film, thin film structure, or solid surface, wherein the probe beam portion is diffracted by material disturbances produced by the excitation beams;
  monitoring coherent interference of a diffracted part of the probe beam portion with the reference beam portion; and
  determining one or more properties of the thin film, thin film structure, or solid surface based at least in part on the monitored coherent interference.

36. The method of claim 35, wherein the one or more measured properties comprises a thin film thickness.

37. The method of claim 35, wherein the one or more measured properties comprises a thickness of multiple films.

38. The method of claim 35, wherein the one or more measured properties comprises dimensions of a structure fabricated on a solid surface.

39. The method of claim 38, wherein the structure is a damascene line array.

40. The method of claim 35, wherein the probe beam portion is the zero order diffraction of the probe beam, and the reference beam portion is the second order diffraction of the probe beam.

41. The method of claim 40, wherein the excitation beam portions are +/−1 diffraction orders of the excitation beam.

* * * * *